(12) United States Patent
Cowley et al.

(10) Patent No.: US 8,577,459 B2
(45) Date of Patent: Nov. 5, 2013

(54) SYSTEM AND METHOD FOR ESTIMATING BATTERY CAPACITY

(75) Inventors: Anthony W. Cowley, Houston, TX (US); Saadat Hussain, Houston, TX (US)

(73) Assignee: Cyberonics, Inc., Houston, TX (US)

(*) Notice: Subject to any disclaimer, the term of this patent is extended or adjusted under 35 U.S.C. 154(b) by 245 days.

(21) Appl. No.: 13/016,510

(22) Filed: Jan. 28, 2011

(65) Prior Publication Data

US 2012/0197341 A1    Aug. 2, 2012

(51) Int. Cl.
*A61N 1/08*    (2006.01)

(52) U.S. Cl.
USPC .......................................................... 607/29

(58) Field of Classification Search
USPC .......................................................... 607/29
See application file for complete search history.

(56) References Cited

U.S. PATENT DOCUMENTS

| | | |
|---|---|---|
| 3,796,221 A | 3/1974 | Hagfors |
| 4,324,251 A | 4/1982 | Mann |
| 4,488,555 A | 12/1984 | Imran |
| 4,556,061 A | 12/1985 | Barreras et al. |
| 4,686,990 A | 8/1987 | Moberg |
| 4,702,254 A | 10/1987 | Zabara |
| 4,715,381 A | 12/1987 | Moberg |
| 4,850,356 A | 7/1989 | Heath |
| 4,867,164 A | 9/1989 | Zabara |
| 4,899,750 A | 2/1990 | Ekwall |
| 4,964,407 A | 10/1990 | Baker, Jr. et al. |
| 5,025,807 A | 6/1991 | Zabara |
| 5,127,404 A | 7/1992 | Wyborny et al. |
| 5,137,020 A | 8/1992 | Wayne et al. |
| 5,137,021 A | 8/1992 | Wayne et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,188,104 A | 2/1993 | Wernicke et al. |
| 5,193,538 A | 3/1993 | Ekwall |
| 5,201,808 A | 4/1993 | Steinhaus et al. |
| 5,201,865 A | 4/1993 | Kuehn |
| 5,215,086 A | 6/1993 | Terry, Jr. et al. |
| 5,222,494 A | 6/1993 | Baker, Jr. |

(Continued)

FOREIGN PATENT DOCUMENTS

| | | |
|---|---|---|
| EP | 1321773 A1 | 6/2003 |
| WO | 0108749 A1 | 2/2001 |
| WO | 2004075982 A1 | 9/2004 |

OTHER PUBLICATIONS

International Patent Application No. PCT/US2011/061609, International Search Report and Written Opinion Dated Jun. 5, 2012, 10 pages.

(Continued)

*Primary Examiner* — Eric D. Bertram
(74) *Attorney, Agent, or Firm* — Cyberonics, Inc.

(57) ABSTRACT

A method for estimating capacity of a battery in an implantable medical device includes obtaining a characteristic curve of voltage versus resistance for the battery, periodically determining voltage and resistance of the battery, and comparing the resistance with a third derivative function of the characteristic curve, the third derivative function having roots representing near depletion of the battery and end of service of the battery, respectively. Remaining time of service of the battery can also be determined by comparing the resistance value with a curve of battery capacity versus resistance for the battery.

20 Claims, 6 Drawing Sheets

(56) References Cited

U.S. PATENT DOCUMENTS

| | | |
|---|---|---|
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,515 A | 7/1994 | Rutecki et al. |
| 5,335,657 A | 8/1994 | Terry, Jr. et al. |
| 5,344,431 A | 9/1994 | Merritt et al. |
| 5,352,962 A | 10/1994 | Galburt |
| 5,352,968 A | 10/1994 | Reni et al. |
| 5,372,607 A | 12/1994 | Stone et al. |
| 5,391,193 A | 2/1995 | Thompson |
| 5,431,692 A | 7/1995 | Hansen et al. |
| 5,458,624 A | 10/1995 | Renirie et al. |
| 5,496,353 A | 3/1996 | Grandjean et al. |
| 5,507,786 A | 4/1996 | Morgan et al. |
| 5,522,865 A | 6/1996 | Schulman et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,620,474 A | 4/1997 | Koopman |
| 5,703,469 A | 12/1997 | Kinoshita |
| 5,707,400 A | 1/1998 | Terry, Jr. et al. |
| 5,713,936 A | 2/1998 | Staub et al. |
| 5,741,307 A | 4/1998 | Kroll |
| 5,741,311 A | 4/1998 | McVenes et al. |
| 5,755,742 A | 5/1998 | Schuelke et al. |
| 5,769,873 A | 6/1998 | Zadeh |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,925,068 A | 7/1999 | Kroll |
| 5,928,272 A | 7/1999 | Adkins et al. |
| 6,016,448 A | 1/2000 | Busacker et al. |
| 6,073,050 A | 6/2000 | Griffith |
| 6,108,579 A | 8/2000 | Snell et al. |
| 6,148,235 A | 11/2000 | Kuiper |
| 6,167,309 A | 12/2000 | Lyden |
| 6,181,969 B1 | 1/2001 | Gord |
| 6,185,461 B1 | 2/2001 | Er |
| 6,212,431 B1 | 4/2001 | Hahn et al. |
| 6,317,633 B1 | 11/2001 | Jorgenson et al. |
| 6,341,236 B1 | 1/2002 | Osorio et al. |
| 6,400,988 B1 | 6/2002 | Gurewitsch |
| 6,445,951 B1 | 9/2002 | Mouchawar |
| 6,453,198 B1 | 9/2002 | Torgerson et al. |
| 6,473,644 B1 | 10/2002 | Terry, Jr. et al. |
| 6,490,484 B2 | 12/2002 | Dooley et al. |
| 6,490,486 B1 | 12/2002 | Bradley |
| 6,553,263 B1 | 4/2003 | Meadows et al. |
| 6,587,719 B1 | 7/2003 | Barrett et al. |
| 6,587,727 B2 | 7/2003 | Osorio et al. |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,654,640 B2 | 11/2003 | Lyden |
| 6,658,294 B1 | 12/2003 | Zadeh et al. |
| 6,671,552 B2 | 12/2003 | Merritt et al. |
| 6,671,556 B2 | 12/2003 | Osorio et al. |
| 6,687,538 B1 | 2/2004 | Hrdlocka et al. |
| 6,721,600 B2 | 4/2004 | Jorgenson et al. |
| 6,745,077 B1 | 6/2004 | Griffith et al. |
| 6,748,273 B1 | 6/2004 | Obel et al. |
| 6,760,624 B2 | 7/2004 | Anderson et al. |
| 6,760,625 B1 | 7/2004 | Kroll |
| 6,804,557 B1 | 10/2004 | Kroll |
| 6,820,019 B1 | 11/2004 | Kelly et al. |
| 2001/0034541 A1 | 10/2001 | Lyden |
| 2002/0022866 A1 | 2/2002 | Borkan |
| 2003/0074037 A1 | 4/2003 | Moore |
| 2004/0039424 A1 | 2/2004 | Merritt et al. |
| 2004/0199146 A1 | 10/2004 | Rogers et al. |
| 2005/0088145 A1 | 4/2005 | Loch |
| 2005/0177206 A1 | 8/2005 | North et al. |
| 2005/0272280 A1 | 12/2005 | Osypka |
| 2007/0150019 A1 | 6/2007 | Youker et al. |
| 2007/0216366 A1 | 9/2007 | Inamine et al. |
| 2008/0097544 A1 | 4/2008 | Gandhi et al. |
| 2010/0121591 A1* | 5/2010 | Hall .............................. 702/63 |

OTHER PUBLICATIONS

Terry, R.S. et al., "The Implantable Neurocybernetic Prosthesis System," Pacing and Clinical Electrophysiology, vol. 14, No. 1, (Jan. 1991), pp. 86-93.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

* cited by examiner

SYSTEM AND METHOD FOR ESTIMATING BATTERY CAPACITY

BACKGROUND OF THE INVENTION

1. Field of the Invention

Noon The present disclosure generally relates to rechargeable battery systems. More particularly, the present disclosure relates to a method for estimating remaining battery capacity using an algorithm based on voltage and battery resistance.

2. Description of the Related Art

In recent years there has been an explosion in the popularity and types of portable electronic devices. Such devices include communication and entertainment devices, such as cell phones, PDA's, portable music and video players and the like, as well as electronic devices that are implantable into a human or animal body, such as pacemakers, implantable drug delivery systems and nerve stimulation devices. These and other types of portable electronic devices generally rely upon electrochemical storage batteries as a power source. Many of these devices use rechargeable batteries, while others use conventional single-use batteries. In either case, however, it can be desirable to have an accurate estimate of remaining battery capacity or battery life in order to know when to recharge or replace the batteries. This is particularly true in the case of implantable electronic devices, where the health of the user may depend upon proper functioning of the device, and the device is not easily accessible, since replacing a battery requires a surgical procedure.

There are various known methods for estimating remaining battery life in electronic devices that are currently used. For example, methods that have been adopted to predict or estimate remaining battery life include the remaining capacity (mA-hr) method, direct energy computation (J), and the coulomb counter (Amps/s) method. Unfortunately, many of these methods rely upon some significant and sometimes inaccurate assumptions, can be moderately to highly complex to implement, and vary widely in accuracy. Ironically, some battery life estimation methods that are currently used are computationally intensive and impose a substantial strain on battery life in the course of computing battery life.

The present disclosure is directed to overcoming, or at least reducing the effects, of one or more of the issues set forth above.

SUMMARY OF THE INVENTION

It has been recognized that it would be advantageous to develop a simple and robust method for estimating remaining battery capacity in an electronic device.

It has also been recognized that it would be advantageous to develop a method for estimating remaining battery capacity in an electronic device that uses only minimal power from the electronic device.

In accordance with one aspect thereof, the present disclosure provides a method for estimating capacity of a battery in an implantable medical device. The method includes obtaining a characteristic curve of voltage versus resistance for the battery, periodically determining voltage and resistance of the battery, and comparing the resistance with a third derivative function of the characteristic curve, the third derivative function having roots representing near depletion of the battery and end of service of the battery, respectively.

In one embodiment, remaining time of service of the battery can also be determined by comparing the resistance value with a curve of battery capacity versus resistance for the battery.

In accordance with another aspect thereof, the present disclosure provides an implantable system, including an implantable device, having a battery, and a battery circuit capable of measuring voltage and calculating a resistance of the battery; and a computer program product, stored in a tangible storage medium. The program produce includes machine-readable instructions for measuring a reference voltage and calculating a resistance value of the battery, comparing the voltage and resistance values with a characteristic curve of resistance versus voltage for the battery, and estimating future performance characteristics of the battery based upon a third derivative of the characteristic curve and a position of the voltage and resistance values thereon. The implantable system further includes an output mechanism, adapted to provide an indication to a user of the future performance characteristics.

In accordance with yet another aspect thereof, the present disclosure provides a method for managing a battery of an implantable device. The method is carried out by a computer, associated with the implantable device, having a microprocessor and digital memory containing machine-readable program instructions for causing the computer to perform the steps of periodically determining a reference voltage and resistance of the battery in the implantable device, comparing the voltage and resistance with a characteristic curve of voltage versus resistance for the battery, creating a modified characteristic curve based upon the voltage and resistance, comparing the voltage and resistance with a third derivative of the modified characteristic curve, the third derivative curve indicating a relative condition of the battery, comparing the resistance with a battery capacity curve, the battery capacity curve indicating remaining power of the battery, and providing an output to a user indicating at least one of the condition of the battery and the remaining power of the battery.

These and other embodiments of the present application will be discussed more fully in the description. The features, functions, and advantages can be achieved independently in various embodiments of the claimed invention, or may be combined in yet other embodiments.

Figure 1:
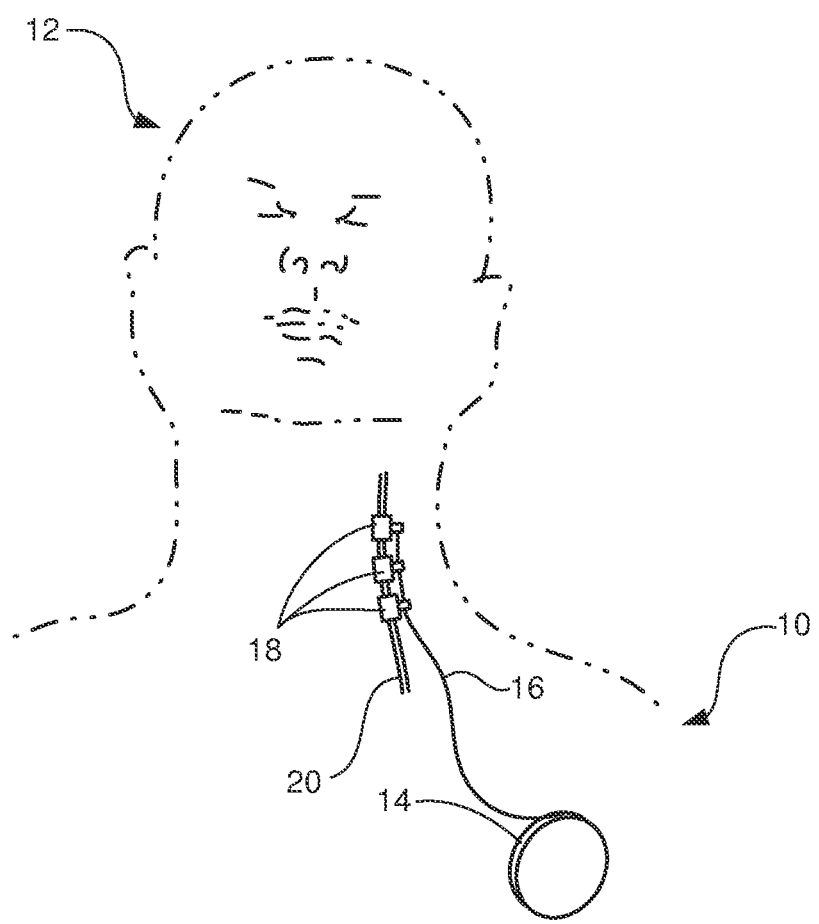
FIG. 1 is a schematic representation of a human subject showing a subcutaneous vagus nerve stimulation system, having a lead extending from a battery-powered pulse generator device to electrodes attached at the left vagus nerve.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DESCRIPTION OF ILLUSTRATIVE EMBODIMENTS

Illustrative embodiments are described below as they might be employed in a method for estimating battery capacity. In the interest of clarity, not all features of an actual implementation are described in this specification. It will be appreciated that in the development of any such actual embodiment, numerous implementation-specific decisions may be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely implanted into a human or animal body, with no portions of the apparatus extending outside the body after implantation.

As used herein, the terms "implantable device" and "implantable medical device" or "IMD" mean any type of electrical device that is implantable into a human or animal body, and is configured to monitor or affect a function of the body. Examples of implantable medical devices include cardiac pacemakers, nerve stimulation devices, and implantable drug delivery devices.

As noted above, there are a variety of battery powered devices in which it is desirable to have an accurate estimate of remaining battery power. In addition to communication and entertainment devices, this includes implantable devices that can be used for monitoring and affecting physiological or biological function of a human or animal body. Such devices include cardiac pacemakers, implantable drug delivery systems, and nerve stimulation devices. Among the latter are implantable devices for vagus nerve stimulation (VNS). VNS was approved by the FDA in 1998 as an adjunctive therapy for epilepsy with partial onset seizures. VNS is achieved through an implanted pulse generator that delivers a bipolar, biphasic pulse to the vagus nerve. The implant procedure is very similar to the implantation of a pacemaker. The generator is implanted subcutaneously, typically in the upper left pectoral region. An electric lead is connected between the pulse generator and one or more electrodes that are attached to the vagus nerve. While the following description presents a system and method for estimating battery life in the context of an implantable vagus nerve stimulation system, this application is only exemplary. It is to be understood that the system and method disclosed herein can be applied to a wide variety of battery-powered electronic devices, and is not limited to the particular exemplary application in which it is shown and described.

Shown in FIG. 1 is a schematic diagram of one embodiment of an implantable vagus nerve stimulation system, indicated generally at 10, implanted into a patient 12. The system includes a pulse generator 14, and a tether or lead 16 that has one or more electrodes 18 at its distal end. The tether and electrodes are collectively referred to as the lead, and the lead provides an interface between the pulse generator 14 and the electrodes 18. The electrodes 18 are attachable to the vagus nerve 20. An implantable VNS system of this type and having these basic features is known to those of skill in the art, and is commercially available, such as from Cyberonics, Inc. of Houston, Tex.

The pulse generator 14 can be a multi-programmable device, which allows a physician to set various parameters of operation of the device. The programmable parameters can include signal amplitude (e.g., 0-3.5 mA), frequency (e.g., 1-30 Hz), pulse width (e.g., 130-1000 µs), signal ON time (e.g., 7-60 sec) and signal OFF time (e.g., 0.2-180 min). It is to be appreciated that these pulse parameters are only exemplary, and that other parameters can also be used. The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 15 Hz frequency, 250 µs pulse width, with a 30 sec ON time, and 5 min OFF time. The variability in parameters allows the physician to adjust for greater efficacy or less severe side effects, depending on the patient.

Figure 2:
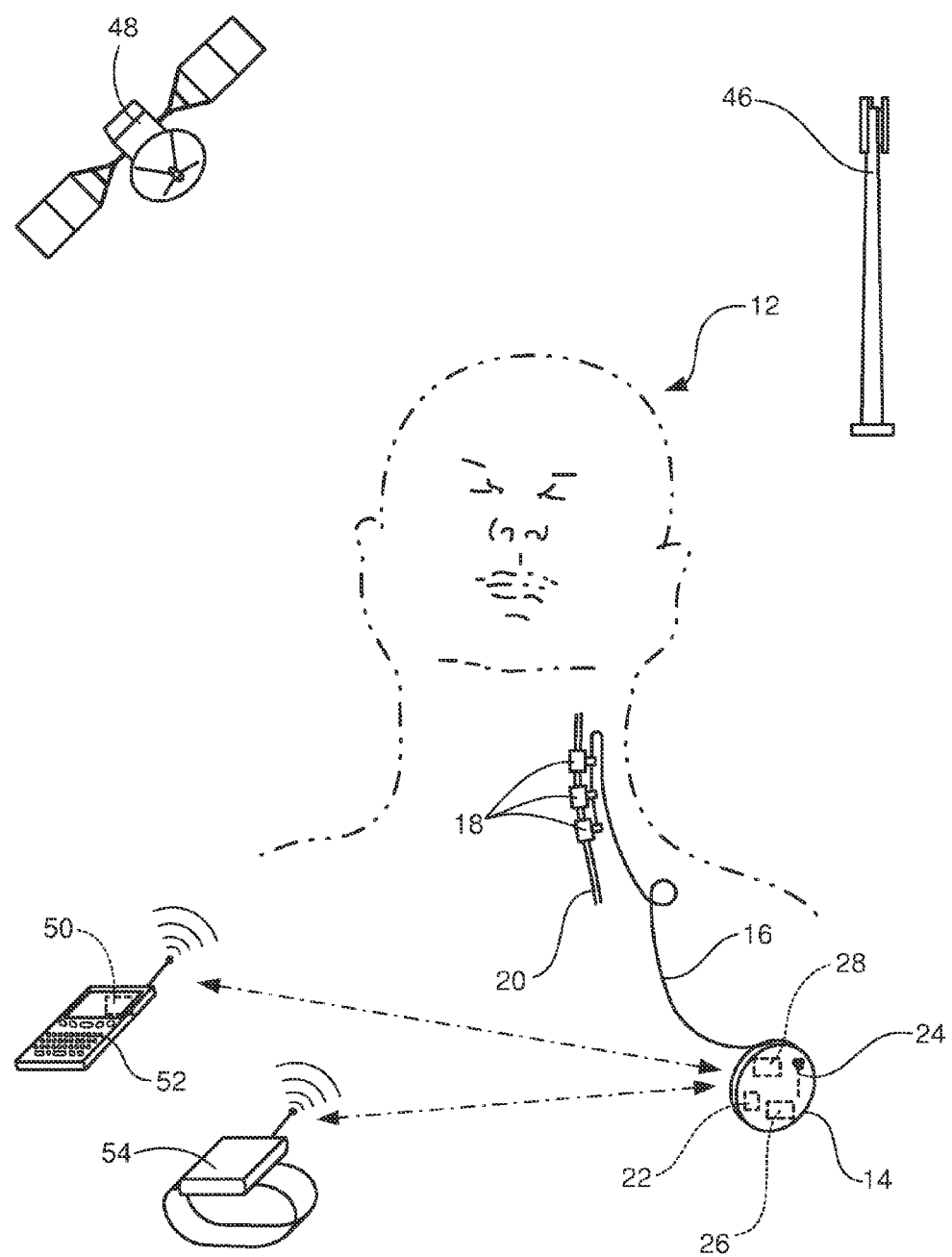
FIG. 2 is a schematic representation of a portion of a battery-powered implantable pulse generator device and a remote handheld computer device in wireless communication with the pulse generator device and configured to compute an estimate of remaining battery capacity in the pulse generator device.

As shown in FIG. 2, the pulse generator 14 can include within its housing a variety of components, including battery 22, an antenna 24, a GPS transceiver 26, and a microprocessor 28 with digital memory. The battery 22 can be a rechargeable battery, and can be configured for periodic inductive recharging, though the components of a recharging system are not shown herein. The antenna 24 is a common element for an implantable device, and can be provided to send and/or receive data and programming and control instructions from an external communications device, as discussed below. This allows the implanted device 14 to receive programming and control instructions from an external communications device, and to transmit data regarding operation of the pulse generation device. Communications and control with implanted devices is well known and widely used. Devices such as pacemakers and the like are routinely programmed and/or controlled via wireless communication methods, such as the Medical Information Communication System protocol (MICS), which uses radio waves to transmit information to and from implanted devices.

Figure 3:
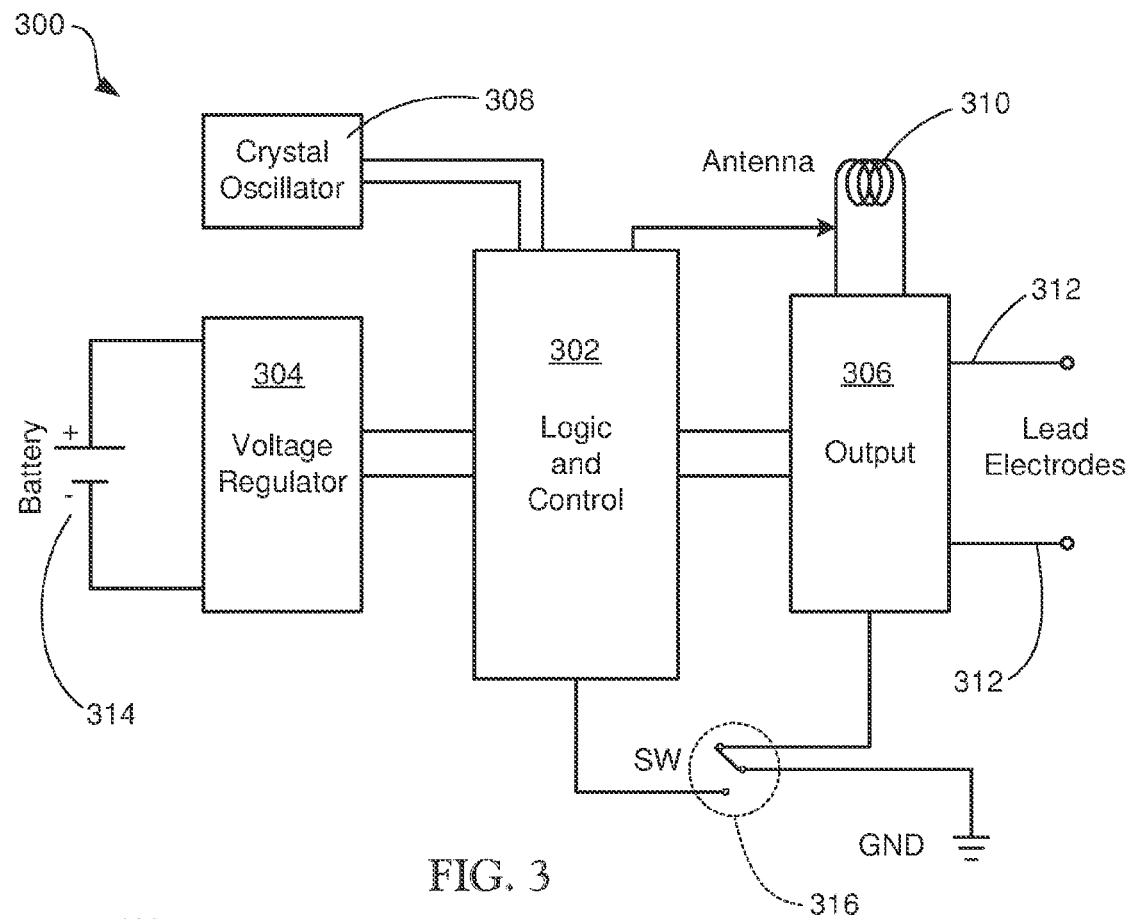
FIG. 3 is a schematic diagram of the internal components of an embodiment of an implantable pulse generator for a VNS system.

A more specific schematic diagram of the internal components of an embodiment of an implantable pulse generator device, indicated generally at 300, is shown in FIG. 3. In this embodiment the pulse generator device includes a logic and control unit 302, a voltage regulator unit 304, an output unit 306 and a crystal oscillator 308. The logic and control unit 302 contains circuitry and programming for control and operation of the pulse generator device 300, along with digital memory for storing programming instructions. The logic and control unit 302 is operatively coupled to an antenna 310, which allows programming and operational data to be transmitted and received by the pulse generator device 300. The antenna 310 is driven by the output unit 306, which also directly provides nerve stimulation signals via the lead electrodes 312.

Also operatively connected to the logic and control unit 302 are the crystal oscillator 308 and the voltage regulator 304. The crystal oscillator 308 provides an accurate time signal for the logic and control unit 302. The voltage regulator 304 controls power input from the battery 314 to the logic and control unit 302. The pulse generator device 300 can also include a reed switch 316 that allows selective connection of the logic and control unit 302 or output unit 306 to ground. This allows the pulse generator device 300 to operate in a secondary magnet mode, delivering a pre-programmed burst of stimulation when activated by an external magnet. While the elements shown in FIG. 3 are illustrated as hardware elements, it is to be recognized and understood that many portions of the pulse generator device 300 can be implemented as firmware, software or the like, and that many combinations are possible.

While a Global Positioning System (GPS) transceiver (26 in FIG. 2) can be incorporated as a specific hardware element in the implanted pulse generation device, one of skill in the art will recognize that GPS functions can be programmed into the logic and control unit 302. As another alternative, a GPS transceiver and/or corresponding programming can be placed in other locations associated with a patient's body. For example, referring back to FIG. 2, a GPS transceiver 50 can be associated with an external PDA or smart phone-type device 52, or a wristwatch or wristwatch-like device 54, or some other external computing device. Other types of wearable or external computing devices can also be used, such as a POCKET PC™, iPhone®, a laptop computer, a special purpose portable computing device, etc. The wristwatch-like device 54 can be considered as one example of a special purpose portable computing device. The external device can function as an activation or input/output device for the implanted device. As such, it can incorporate an output mechanism for providing indications to the user of aspects of operation of the implanted device (e.g. operational parameters, errors, battery condition, etc.). The output mechanism can provide indications such as indicator lights, alphanumeric indications, icons, audible alerts, etc. The implanted device itself can also include an output mechanism in the form of an audible alert which can be heard outside the body. Such an alert can be useful for noting error conditions, battery depletion, etc.

The smart phone 52 and wristwatch device 54 are shown in FIG. 2 with antennas, which are intended to represent the wireless communications capability of the devices, rather than the shape or position of an actual antenna structure. The antenna allows the external device to receive signals from a cellular or other mobile telephone system, represented by the cellular tower 46, or from satellites 48, or other communications system. The external device can be configured to transmit data to the pulse generation device 14 using Bluetooth or some other wireless transmission protocol, for example.

Performing various computational operations and/or having various hardware components included within a device other than the pulse generation device 14 can be desirable for power conservation. For example, power-hungry microprocessing tasks and analysis can be transferred to the external device, rather than being performed by the microprocessor 28 of the pulse generation device, with the results of those microprocessing tasks transmitted back to the implanted device. This can conserve power for the implanted device. Similarly, having an external GPS transceiver and associated microprocessor can also reduce power demands on the implanted pulse generator. A GPS transceiver that is in substantially constant communication with a GPS satellite system and a microprocessor that analyzes the positional information can use significant power, which is at a premium with implanted devices.

One microprocessing task that can be performed by an external device in communication with a battery powered device is computation of battery life. As noted above, it is desirable to have an accurate estimate of remaining battery power and battery life for a battery-powered electronic device. This is of particular interest for implanted devices, since the health of the user may depend upon the device, and direct access to the battery generally requires a surgical procedure. Thus, for example, the microprocessor associated with a smart phone 52 or wristwatch device 54 or some other external device can be programmed to receive battery data measurements (e.g. open circuit voltage), transmitted from the pulse generator 14, and perform the analysis to estimate remaining battery life. The external device can then transmit battery information, operational commands or other information to the pulse generation device 14 or some other device.

Figure 4:
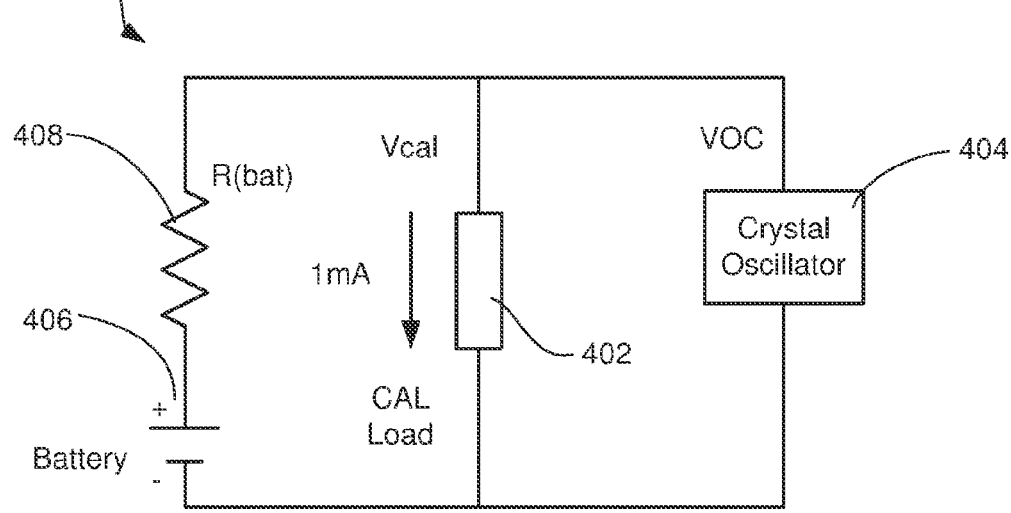
FIG. 4 is a schematic diagram of a battery circuit associated with the pulse generator of FIG. 3, which can be used to detect open circuit voltage of the battery.

Advantageously, a method has been developed for more accurately estimating battery capacity in an electronic device, such as an implanted pulse generator device like that shown in FIGS. 1-2. The method disclosed herein provides an adaptive algorithm to estimate time to battery depletion based on battery terminal voltage and battery resistance. Shown in FIG. 4 is a schematic diagram of a theoretical battery circuit 400 for a pulse generator or other battery powered device, for measuring open circuit voltage and battery resistance. As an electronic storage battery becomes depleted, its internal resistance will increase. The battery circuit shown in FIG. 4 includes a load element 402, which represents the total electrical load imposed upon the battery by the device. The battery circuit 400 also includes a crystal oscillator 404, which provides a time signal. The internal resistance $R_{bat}$ of the battery 406 is represented by a resistor 408. This battery circuit can be used to determine the resistance $R_{bat}$ of the battery based upon the following equation:

$$R_{bat} = (V_{ref} - V_{cal})/I_{cal} \quad [1]$$

In this equation, $V_{ref}$ is the reference voltage for the battery, $V_{cal}$ is the load voltage, and $I_{cal}$ is the load current. The reference voltage $V_{ref}$ can be one of several voltages, including open circuit voltage $V_{oc}$ (as labeled in FIG. 4), a low power mode voltage, or a voltage measured at a predefined operating mode, for example. Based on direct measurement of the reference voltage and load voltage and current, using this equation the internal resistance or impedance of a battery can be determined.

By measuring the reference voltage and calculating the battery resistance of a given battery over its useful life in a given device having a given load and load current, a graph of voltage versus resistance or impedance can be plotted. A graph showing multiple experimentally-obtained curves 500a-f of impedance versus reference voltage for a particular battery is provided in FIG. 5. These curves are exemplary of curves obtained through extensive bench testing of many batteries, with a polynomial fit applied to the results. That is, a group of batteries of a given type were successively placed in a particular device, and their voltage and impedance were plotted over the entire life of the battery. As can be seen in the graph of FIG. 5, each battery can be expected to produce a slightly different curve because of variations in materials, manufacturing tolerances, etc.

Figure 5:
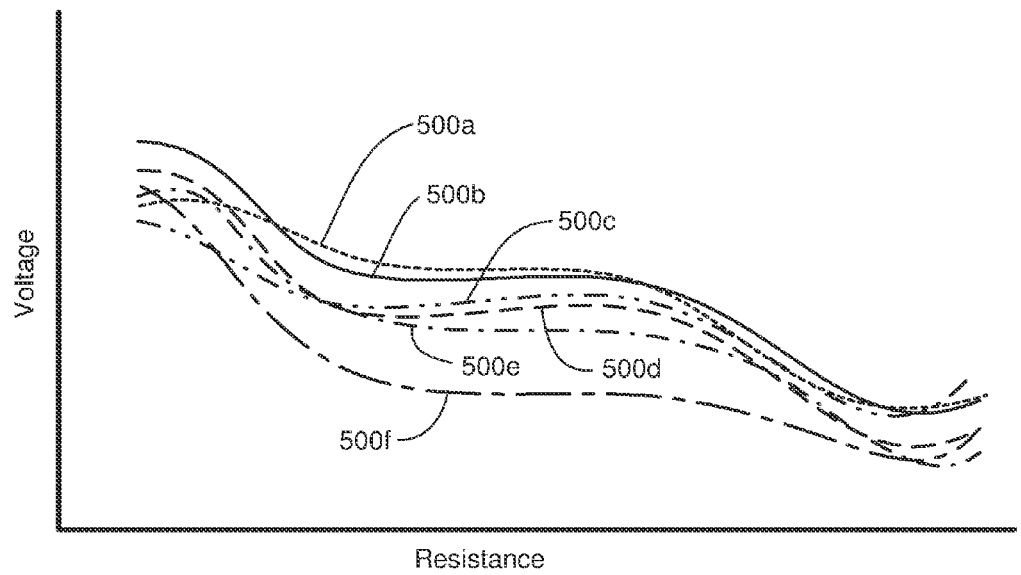
FIG. 5 is a graph showing multiple experimentally obtained curves of impedance versus open circuit voltage for a particular battery.
Figure 6:
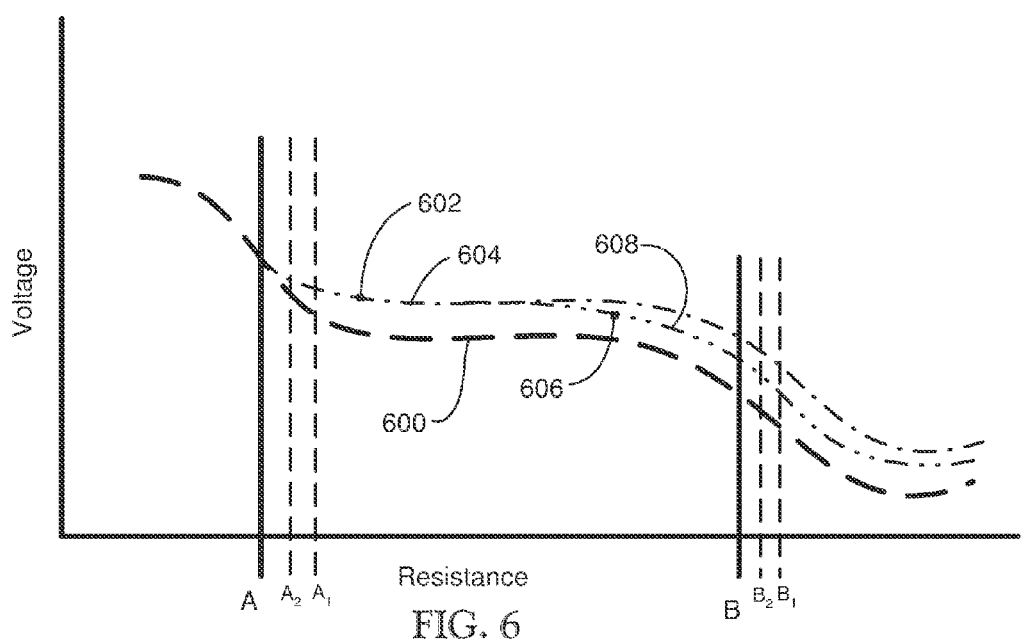
FIG. 6 is an exemplary characteristic graph of impedance versus open circuit voltage for a given battery type based upon multiple experimentally obtained curves of impedance versus open circuit voltage for that type of battery.

Based upon the multiple experimentally-obtained curves 500 shown in FIG. 5, a characteristic curve of impedance versus open circuit voltage can be determined for that battery type and size. Such a characteristic curve 600 is provided in FIG. 6. The characteristic curve 600 can be obtained by averaging (or combining through some other statistical measure of central tendency) the ordinate values of all of the voltage-resistance curves 500 that were experimentally obtained in FIG. 5. The curve in FIG. 6 is an exemplary characteristic graph of impedance versus voltage for a given battery type based upon multiple experimentally obtained curves of impedance versus voltage for that type of battery. In actual practice, the characteristic curve can be extracted from data provided by the battery manufacturer. Based on numerical analysis, it has been found that this characteristic curve is a $5^{th}$ order polynomial.

Once the characteristic curve is created, it is stored in memory, such as in the pulse generator (14 in FIG. 1) or in an external device (52 in FIG. 2). When the device (e.g. the pulse generator device 14 in FIG. 1) first begins using a particular battery, the battery is initially presumed to function according to the characteristic curve 600. However, as shown in FIG. 5, each battery is slightly different. Consequently, under the method disclosed herein, the electronic device periodically measures the voltage, calculates the resistance, and replaces the characteristic points on the graph 600 with measured data for that specific battery. The system can then recalculate or extrapolate the $5^{th}$ order polynomial curve to provide an estimate of the future voltage-resistance relationship. For example, as shown in FIG. 6, if after the initial characteristic curve 600 is plotted a new data point 602 representing directly determined voltage and resistance of the battery is obtained, the system can recalculate the curve and recognize a new, adapted or modified curve 604. Because of its slightly different characteristics, this new curve will indicate slightly different indicator points $A_1$ and $B_1$. From this point forward, the new, adapted curve 604 will be used for battery capacity estimation, rather than the original presumed characteristic curve 600. Later, when another new data point 606 is determined, the curve recalculation can be performed again to predict a new curve 608, which will suggest revised indicator points $A_2$ and $B_2$, in the same manner. This process can repeat over and over throughout the life of the battery.

As a result of this process, the characteristic curve 600 is repeatedly modified to create an adapted curve, which better reflects the performance of the actual battery within the device, instead of the averaged, characteristic data. Consequently, the voltage-resistance relationship estimate will become more accurate over time.

Figure 7:
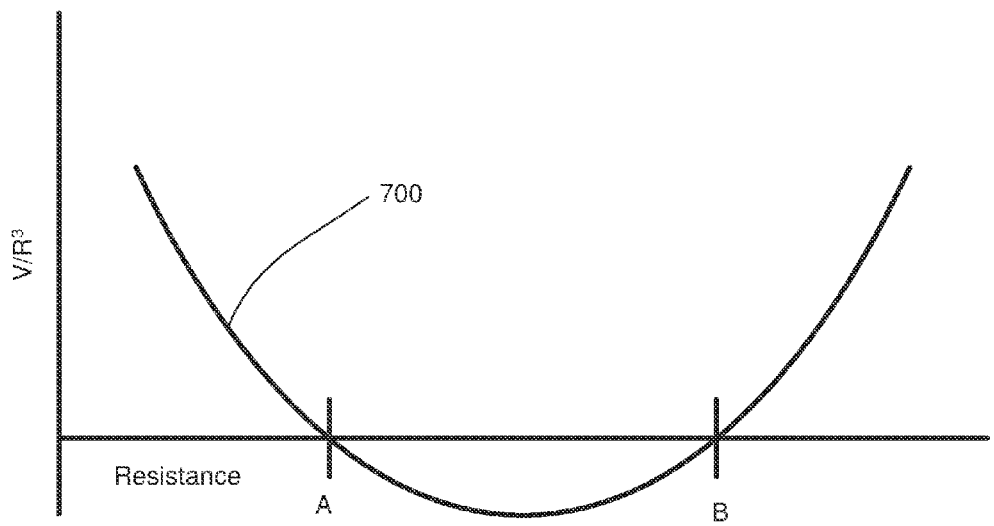
FIG. 7 is a graph of the third derivative of the baseline curve of FIG. 3, showing the roots of the function which correspond to key points in the baseline curve.

The indicator points A and B on the resistance/voltage curve are of particular interest. These are the points at which the curvature changes. Point A may serve as a warning that the battery is near depletion (e.g., declaring an elective replacement indicator (ERI) flag). Point B can represent end of service (EOS) of the battery. The locations of these changes in curvature can be found by taking the $3^{rd}$ derivative of the characteristic curve, and finding the points where the $3^{rd}$ derivative changes from positive to negative (for the first curvature change) and from negative to positive (for the second curvature change). A graph of the third derivative curve 700 of the baseline curve of FIG. 6, showing the roots or zero points A and B of the function which correspond to key points A and B in the baseline curve 600, is provided in FIG. 7.

Figure 8:
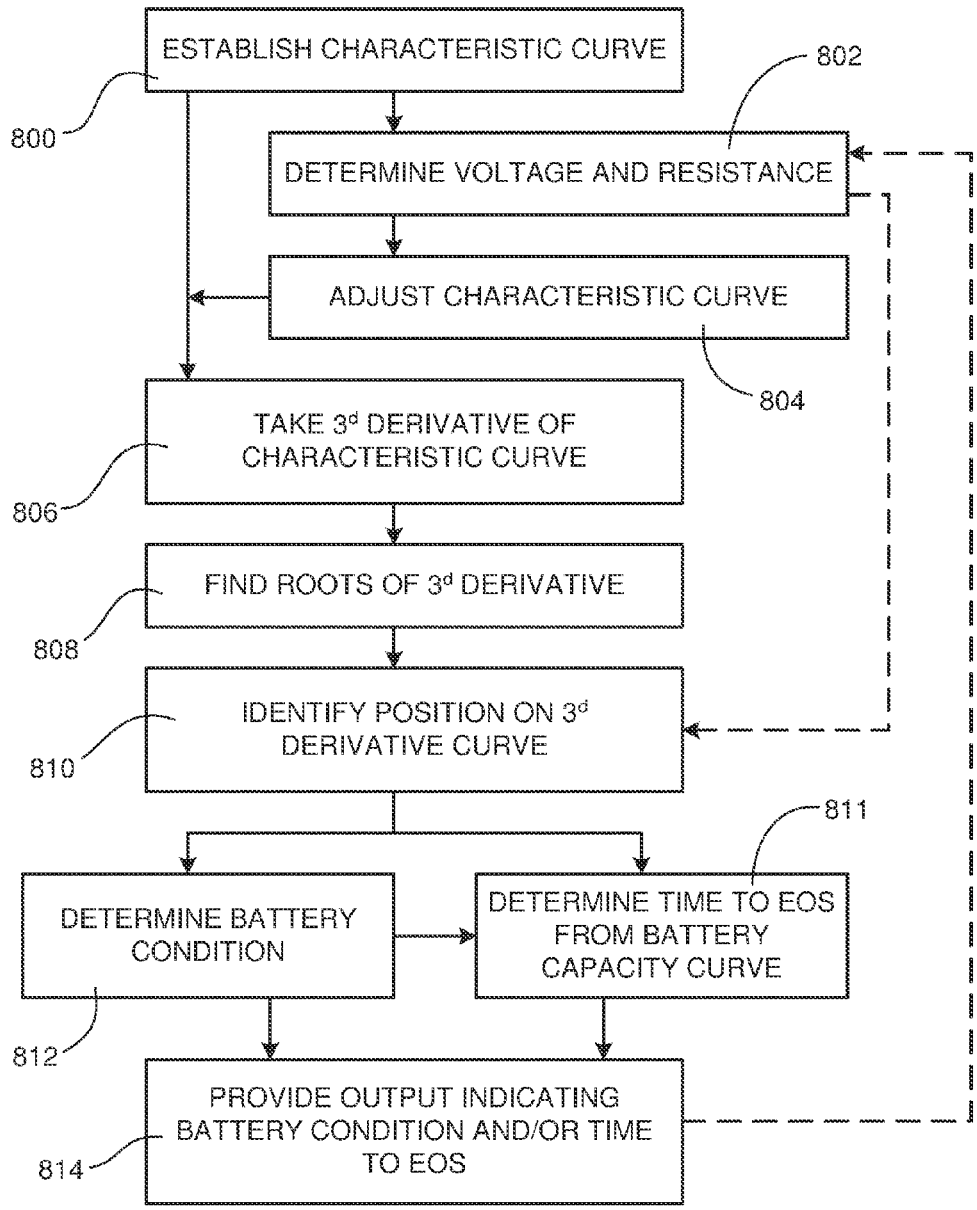
FIG. 8 is a flowchart outlining the steps in one embodiment of a method for estimating battery capacity in accordance with the present disclosure.

FIG. 8 is a flowchart outlining one embodiment of a method for estimating battery capacity in accordance with the present disclosure. First, a characteristic curve of resistance vs. voltage is obtained and stored within the device (800). This is a curve like that shown in FIG. 6. The characteristic curve can be established in at least a couple of ways. It can be obtained from the battery manufacturer, or it can be derived by experimentally plotting and averaging multiple curves of resistance versus voltage for a representative sample of batteries. A polynomial curve is numerically fit to the experimental data, and the resulting characteristic curve is then stored in memory.

Once the characteristic curve has been established and the battery installed in the electronic device, periodic determinations of voltage and resistance are made on the device (802) and these values are used to update the characteristic curve (804) with new data points. That is, with each measurement, a new data point representing the newly determined voltage and resistance is plotted and compared to the prior curve. The difference between the new value and the value predicted by the curve allows the numerical estimation of a new trend for the curve, allowing the curve to be modified in view of the new trend. Once again, the computations for this curve modification can be carried out by the external device. Adapting the curve in this manner with actual values allows the estimate to become continuously more accurate over time. The adjusted characteristic curve is also stored in memory, and is used for further estimation.

The indicator points of the adaptive algorithm are determined by the location of the changes in curvature of the characteristic curve. In order to find these change points, the third derivative of the adapted characteristic curve is taken (806). These change points can be determined by finding the roots of the third derivative (808) of the polynomial curve. That is, the curvature change at "A" in FIG. 6 corresponds to the root point "A" of the third derivative curve in FIG. 7. Similarly, the curvature change at "B" in FIG. 6 corresponds to the root point "B" of the third derivative curve in FIG. 7. Reaching point A signifies that the battery is approaching depletion, and "B" signifies end of service (EOS) of the battery.

Once the roots of the third derivative curve have been determined, the next step is to determine where on that curve the battery's current condition lies (810). This involves using the resistance information from 802 to find the corresponding point on the third derivative curve. The position of a point along the third derivative curve allows one to identify whether the battery is before ERI (the near depletion point A), between ERI (point A) and EOS (point B), or has passed EOS. The relative position along this curve thus gives a general or rough indication of the battery condition (812)—that is, whether the battery has not yet reached a near depletion state, has passed the near depletion point but not yet reached end of service, or whether the battery has passed the end of service position. This battery condition indication by itself can be provided to a user through some output device, such as an indicator light, an alphanumeric display, an iconic display, etc. (814).

Figure 9:
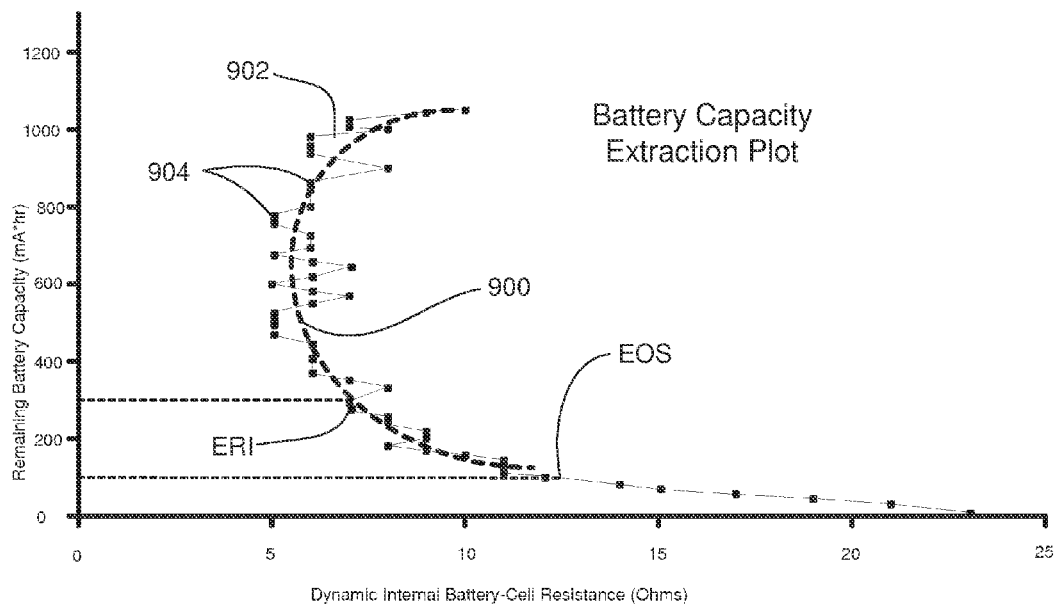
FIG. 9 is a graph of remaining battery capacity versus dynamic internal battery-cell resistance for a given battery.

Comparing the battery's voltage and resistance to the third derivative curve only allows for a determination of whether the battery is close to being depleted (ERI) or EOS has been reached. In order to determine battery capacity, a second curve of resistance vs. capacity is compared to the resistance value obtained from the updated characteristic resistance vs. voltage curve. As indicated by the arrows in FIG. 8, in addition to or instead of providing the rough determination of battery condition that the third derivative curve provides alone (812), the system can proceed to 811, which allows one to estimate the remaining battery life by comparing the calculated battery resistance with a battery capacity versus battery resistance curve determined by empirical data from samples of the given battery. FIG. 9 illustrates an example of a plot of battery capacity (measured in milliamp-hours) versus the internal battery cell resistance (Ohms). This is a curve that can be obtained from a battery manufacturer, and can provide a battery characterization having a total distribution variation of +/−3-Sigma. Empirical battery capacity curve 900 is created by measuring the battery capacity versus battery resistance for numerous batteries with the same chemistry and construction, and providing a large number of data points 904. Directly connected together, these data points produce a measured battery capacity curve 902 that is somewhat jagged. However, smoothing of the data allows the creation of the single line battery capacity curve 900, which provides a close approximation of the measured curve.

The value of the battery resistance calculated in 802 can then be found along the horizontal axis of the graph of FIG. 9, and used to find the corresponding point on the curve 900, which will indicate a remaining battery capacity value indicated on the vertical axis in milliamp-hours (mA-hr). The curve 900 provides two battery capacity values for a range of resistance values (as can be seen from the upper and lower portions of the curve 900). This is because internal resistance tends to drop during the early life of a battery, then increase during the later part of the battery's life. However, the relative proximity to the ERI and EOS points (determined in 810) can provide an indication of which portion of the curve to use. For example, if the calculated resistance is 8 Ohms and the system has determined in 812 that the battery has passed the near depletion or ERI point, the corresponding point on the battery capacity curve will indicate a remaining capacity of about 200 mA-hr (rather than approximately 1000 mA-hr). Other rough measures of relative battery usage, such as a coulomb counter or time counter, can also be used to determine the portion of the curve 900 that applies in any given circumstance.

Once the battery capacity has been determined in 811, a suitable output indicating the remaining battery capacity can be provided to a user (814). This output can be via a digital screen, indicator lights, icons, or other types of indicia. Further, this output can indicate the amount of battery life consumed or remaining using time estimates, percentage estimates, or icons depicting the condition of the battery. The output provided in 814 can include the rough battery condition determined in 812, or the actual remaining capacity of the battery determined in 811, or both. For example, if the battery's condition has not yet reached point A, the battery will not yet be at the near depletion point, and a suitable icon can be displayed showing just the rough battery condition determined in 812. On the other hand, at any point during the battery's life, an indication of remaining milliamp hours or percent of total capacity, as determined in 811, can be displayed using an iconic display or alphanumeric display, for example. As another example, if the battery's condition has passed point A but not yet reached point B, as determined at 812, the battery is past the near depletion (ERI) point, but not yet at end of service, and a suitable icon can be displayed, along with an indication of remaining milliamp hours (or percent of capacity) remaining, as determined in 811. Once reaching point B, the battery is depleted, and may have only enough power to provide the battery indication itself, and perhaps maintain memory, without providing any power for operation of the device. At this point a dead battery icon can be displayed. At any time during the life of the battery, an estimate of the general condition of the battery (812) and/or and estimate of time remaining before end of service (EOS) can be made (811), and these estimates can be provided to a user, such as via a digital screen, etc. The time estimate can be in terms of remaining milliamp hours or in terms of days or hours of service, for example.

This battery capacity estimation method, while initially based on characteristic battery data, is adjusted over time to better represent the individual battery in the device. By using an adaptive algorithm, the remaining battery capacity and time to estimated depletion can be determined more accurately. Also, the adjusted characteristic curve becomes more accurate over time, providing a better estimate of remaining capacity when most important, near the end of service.

Advantageously, in an implantable device, the only functions performed on the device can be the measurement of actual voltage and the calculation of battery resistance and storage of the determined data points. The external device (e.g. a handheld computer) can store the baseline curve (FIG. 5), which is common to all batteries of a given type. As the new data points (voltage and resistance) are transmitted, the handheld computer can perform the update to the baseline curve (FIG. 5) and store the modified curve (FIG. 6), derivative calculation (FIG. 7), and estimated time to battery depletion computations. The handheld device can also store the resistance vs. battery capacity characteristic curve (FIG. 9), which has been extracted from manufacturer's provided data, and can be used as a common reference for all batteries.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various vehicle components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method comprising:
   accessing, at a computing device, data indicating a characteristic relationship between voltage and resistance for a battery of an implantable medical device;
   determining, at the computing device, a voltage value and a resistance value of the battery during a first time interval;
   comparing, at the computing device, the resistance value to one or more values indicated by a third derivative function based on the data indicating the characteristic relationship, wherein the data further indicates a first period corresponding to near depletion of the battery and a second period corresponding to end of service of the battery, and wherein the first period and the second period are based on the third derivative function; and
   estimating, at the computing device, one or more future performance characteristics of the battery based on a comparison of the resistance value to the one or more values indicated by the third derivative function.

2. The method of claim 1, wherein the data indicating the characteristic relationship is stored in a memory of the computing device.

3. The method of claim 1, wherein the computing device includes a personal digital assistant device, a smartphone, a laptop computing device, or a portable computing device.

4. The method of claim 1, further comprising:
determining a second voltage value and a second resistance value of the battery during a second time interval;
comparing the second resistance value to the data indicating the characteristic relationship;
creating second data indicating an adapted characteristic relationship between the voltage and the resistance of the battery based on a difference between the resistance value and the second resistance value in the battery; and
comparing the second resistance value with one or more second values indicated by a third derivative function based on the second data indicating the adapted characteristic relationship.

5. The method of claim 1, further comprising providing output to a display device indicating a capacity of the battery relative to the first period, the second period, or both, based on comparing the resistance value to the one or more values indicated by the third derivative function.

6. The method of claim 5, further comprising:
comparing the resistance value to one or more second values indicating a battery capacity relationship; and
determining an estimate of time until the end of service of the battery is reached.

7. The method of claim 1, further comprising:
comparing the resistance value to one or more second values indicating a battery capacity relationship; and
determining an estimate of time until the end of service of the battery is reached.

8. The method of claim 1, wherein the characteristic relationship is determined based on a statistical measure of a plurality of battery characteristic relationships, each corresponding to one of a plurality of batteries that is of a same battery type as the battery of the implantable medical device, wherein each of the plurality of battery characteristic relationships is determined based on a relationship between a measured voltage and a measured resistance of one of the plurality of batteries.

9. The method of claim 1, wherein the voltage value is based on an open circuit voltage, a low power mode voltage, a voltage measured at a pre-defined operating mode, or a combination thereof.

10. A computing device comprising:
a processor; and
a memory accessible to the processor, the memory including instructions that, when executed by the processor, cause the processor to:
access data indicating a characteristic relationship between voltage and resistance for a battery of an implantable device;
determine a voltage value and a resistance value of the battery during a first time interval;
compare the resistance value to one or more values indicated by a third derivative function based on the data indicating the characteristic relationship, wherein the data further indicates a first period corresponding to near depletion of the battery and a second period corresponding to end of service of the battery, and wherein the first period and the second period are based on the third derivative function; and
estimate one or more future performance characteristics of the battery based on a comparison of the resistance values to the one or more values indicated by the third derivative function.

11. The computing device of claim 10, wherein determining the voltage value and the resistance value includes receiving the voltage value and the resistance value from the implantable device via wireless communication.

12. The computing device of claim 11, wherein the computing device includes a personal digital assistant device, a smartphone, a laptop computing device, or a portable computing device.

13. The computing device of claim 10, wherein the instructions further cause the processor to:
create second data indicating a modified characteristic relationship between the voltage and the resistance of the battery; and
estimate one or more second future performance characteristics of the battery based on comparing the resistance value to one or more second values indicated by a third derivative function of the modified characteristic relationship.

14. The computing device of claim 10, wherein the instructions further cause the processor to compare the resistance value to second data indicating a relationship associated with battery capacity of the battery, wherein the one or more future performance characteristics indicate an amount of time until end of service of the battery is reached.

15. The computing device of claim 10, wherein the one or more future performance characteristics of the battery indicate a first amount of time until depletion of the battery is reached and a second amount of time until end of service of the battery is reached.

16. The computing device of claim 10, wherein the memory and the processor are included in the implantable device, the implantable device including a pulse generator of a vagus nerve stimulation system.

17. A tangible computer-readable storage device including instructions that, when executed by a processor, cause the processor to:
access data indicating a characteristic relationship between voltage and resistance for a battery of an implantable device;
determine a voltage value and a resistance value of the battery in the implantable device during a first time interval;
compare the resistance value to one or more values indicated by a third derivative function based on the data indicating the characteristic relationship, wherein the data further indicates a first period corresponding to near depletion of the battery and a second period corresponding to end of service of the battery, and wherein the first period and the second period are based on the third derivative function; and
estimate one or more future performance characteristics of the battery based on a comparison of the resistance value to the one or more values indicated by the third derivative function.

18. The tangible computer-readable storage device of claim 17, wherein an output indicating power remaining in the battery indicates a first amount of time until near depletion of the battery is reached, and a second amount of time until end of service of the battery is reached.

19. The tangible computer-readable storage device of claim 18, wherein the first amount of time is determined based on the first period and the second amount of time determined based on the second period.

20. The tangible computer-readable storage device of claim 17, wherein the instructions further cause the processor to:
- create second data indicating a modified characteristic relationship between the voltage and the resistance of the battery;
- compare the resistance value to one or more second values indicated by a third derivative function based on the second data indicating the modified characteristic relationship;
- compare the resistance value to one or more third values indicating a battery capacity relationship, the battery capacity relationship indicating power remaining in the battery; and
- provide an output to an output device indicating a condition of the battery, the power remaining in the battery, or both.

* * * * *